United States Patent [19]

Barnett et al.

[11] Patent Number: 4,760,029

[45] Date of Patent: Jul. 26, 1988

[54] ASSAY FOR D-1 ANTAGONISTIC ACTIVITY OF NEUROLEPTIC DRUGS

[75] Inventors: Allen Barnett, Pine Brook; William Billard, Scotch Plains; Louis Iorio, Lebanon, all of N.J.

[73] Assignee: Schering Corporation, Kenilworth, N.J.

[21] Appl. No.: 672,744

[22] Filed: Nov. 19, 1984

[51] Int. Cl.[4] .................. G01N 33/566; G01N 33/567
[52] U.S. Cl. .................................... 436/504; 436/501; 436/503; 436/804; 436/815; 540/504
[58] Field of Search ............... 436/501, 503, 504, 804, 436/815; 540/504

[56] References Cited

PUBLICATIONS

Billard, W. et al., Life Sciences, 35:1885–1893, (1984).
Hyttel, J., (1983), Eur. Jour. Pharm., 91:153–154.
Billard, W., et al., (1984), Chem. Abstr., vol. 101: abstract No. 184777s.

*Primary Examiner*—Sidney Marantz
*Assistant Examiner*—Jack Spiegel
*Attorney, Agent, or Firm*—Richard C. Billups; James R. Nelson; Stephen I. Miller

[57] ABSTRACT

A method, reagents, and kit for determining the levels of D-1 receptor antagonistic activity of neuroleptic drugs. The method correlates competition between analyte and tritiated R-(+)-8-chloro-2,3,4,5-tetrahydro-3-methyl-5-phenyl-1H-3-benzazepin-7-ol for binding to D-1 receptors in mammalian brain tissue.

2 Claims, No Drawings

ASSAY FOR D-1 ANTAGONISTIC ACTIVITY OF NEUROLEPTIC DRUGS

BACKGROUND OF THE INVENTION

A report in the recent literature has described the selective dopamine D-1 receptor binding properties of R-(+)-8-chloro-2,3,4,5-tetrahydro-3-methyl-5-phenyl-1H-3-benzazepin-7-ol [J. Pharmacol. Exp. Ther., 226, 462 (1983)]. This selectivity is reported to be 2500 fold or virtually to the exclusion of the dopamine D-2 receptors. Such specificity indicates that the compound may possess novel antipsychotic effects and low liability for producing side effects such as extrapyramidal effects in humans. This is so because D-1 receptor antagonism like D-2 receptor antagonism is associated with antipsychotic effects in laboratory animal models but D-2 receptor antagonism is also associated with the untoward side-effects characteristic of most known neuroleptics (e.g., hyperprolactinemia in animals and humans).

The compound's high specificity for the dopamine D-1 receptor is a novel feature and is unlike standard neuroleptics. This novel feature makes the compound ideally suited for identifying other candidates for their potential as antipsychotic drugs.

SUMMARY OF THE INVENTION

The invention sought to be patented in the form of a kit, is a kit useful for estimating the levels of a neuroleptic drug which is a potent D-1 antagonist present in mammalian plasma; said kit comprising:

(a) A sample of purified mammalian brain tissue and;

(b) A sufficient amount of R-(+)-8-chloro-2,3,4,5-tetrahydro-3-methyl-5-phenyl-1H-3-benzazepin-7-ol to perform one analytic procedure.

In a preferred kit of the invention, the R-(+)-8-chloro-2,3,4,5-tetrahydro-3-methyl-5-phenyl-1H-3-benzazepin-7-ol will be comprised of an enriched level of radioactive atoms in order to facilitate the measurement of the relative binding affinity values.

In a more preferred kit of the invention, the R-(+)-8-chloro-2,3,4,5-tetrahydro-3-methyl-5-phenyl-1H-3-benzazepin-7-ol will be comprised of an enriched level of tritium ($^3$H) atoms located on the 3-methyl substituent.

DETAILED DESCRIPTION OF THE INVENTION

The compound, R-(+)-8-chloro-2,3,4,5-tetrahydro-3-methyl-5-phenyl-1H-3-benzazepin-7-ol (hereinafter referred to as Compound may be prepared by method as described in U.S. Pat. No. 3,393,192 or by other art recognized methods. The Compound possesses in vivo and in vitro antidopaminergic effects markedly different than those of standard antipsychotic drugs. For example, the Compound manifested potent blockade of dopamine stimulated adenylate cyclase but only weak displacement of $^3$H-spiperone binding and no prolactinemia. Based on these results the Compound was postulated to be a selective D-1 receptor antagonist [J. Pharmacol. Exp. Ther., 226, 462 (1983) which is incorporated herein by reference].

The best available ligands used to label the D-1 receptor up to now have been the thioxanthene neuroleptics, $^3$H-cis-(Z)-flupentixol, and $^3$H-cis-(Z)-piflutixol, which show similar affinities for D-1 and D-2 sites [Prog. Neuro-Psychopharmac. 2, 329(1978); Psychopharmacology 67, 107(1980); Life Sciences 28, 563(1981); Life Sciences 33, 2179(1983)].

When the Compound was evaluated for its ability to inhibit $^3$H-cis-(Z)-piflutixol binding, it was found to be very potent and also selective for D-1 sites based on the 700-fold higher concentrations of the drug necessary to inhibit binding of the D-2 selective radioligand, $^3$H-spiperone [Eur. J. Pharmacol. 91, 153(1983)].

Because of this unique profile and a recognition of the potential utility and advantages of a radiolabelled form of the Compound over $^3$H-cis-(Z)-piflutixol as a specific D-1 receptor ligand, [N-methyl-$^3$H] Compound was synthesized. The studies described here were undertaken to characterize the binding properties of [N-methyl-$^3$H] Compound in rat striatum and to define its specificity based on competition studies with selected drugs. The methods and supporting data are described in a paper by B. Billard and colleagues (Life Sciences 35, 1885 (1984), which is incorporated herein by reference.

Tissue Preparation

Male Sprague-Dawley rats (200 to 250 g) from Charles River Breeding Laboratories, Mass. were used to obtain brain tissue. The rats were decapitated, their brains removed and place on ice. Striatal tissue was excised, pooled, and homogenized (Brinkman Polytron, 10 sec) in 100 volumes (v/v) of ice cold 50 mM Tris buffer, pH 7.4 (at 25° C.). The homogenate was centrifuged at 20,000 xg for 10 min. The resultant pellet was rehomogenized in Tris buffer and centrifuged again. The final pellet was resuspended in 50 mM Tris buffer pH 7.4 containing 120 mM NaCl, 5 mM KCL, 2 mM $CaCl_2$, and 1 mM $MgCl_2$ (7).

Assay

Polypropylene incubation tubes (in triplicate) received 100 µl of various concentrations of drugs dissolved or suspended in 0.05 M Tris buffer, pH 7.4, containing 4 mg/ml methylcellulose, 100 µl of a solution of [N-methyl-$^3$H] Compound in Tris buffer (final reaction mixture concentration=0.3 nM) or 100 µl of a solution of $^3$H-spiperone in Tris buffer (final reaction mixture concentration=0.2 nM) and 800 µl of tissue suspension (3 mg/assay). At a ligand concentration of 0.3 nM, binding was found in preliminary experiments to be a linear function of tissue concentration up to 8 mg per assay. Tubes were incubated at 37° C. for 15 min and rapidly filtered under vacuum through Whatman GF/B filters with four 4-ml rinses of ice-cold 50 mM Tris buffer, pH 7.4. The filters were monitored for radioactivity through liquid scintillation counting in Scintosol (Isolab, Inc.).

Results

Parameters of [N-methyl-$^3$H] Compound Binding in Rat Striatum

When binding was evaluated as a function of radioligand concentration, saturation of specific sites was clearly achieved while non-specific binding was minimal.

A competition experiment was performed in which unlabelled Compound at concentrations from 1 pM to 100 nM was allowed to compete with a fixed concentration of [N-methyl-$^3$H] Compound. A Hill plot analysis of the amount of radiolabel bound as a function of the concentration of unlabelled Compound yielded a slope (Hill coefficient) of 1.02. A similar competition experiment with (+) butaclamol also yielded a Hill coefficient of unity. In line with the results obtained with unlabelled Compound, the percentage of radioligand for which (+) butaclamol did not compete was about 5%.

When the competition experiment data for unlabelled Compound bound (labelled+unlabelled) as a function of total amount Compound present, a $K_D$ of 0.27 nM was obtained.

To test further the receptor specificity of [N-methyl-$^3$H] Compound, additional competition curves were generated for a variety of pharmacologically active drugs using both [N-methyl-$^3$H] Compound and $^3$H-spiperone as radioligands. The most potent compound inhibiting [N-methyl-$^3$H] Compound binding was itself. The effects were stereoselective as evidenced by the greatly reduced potency of the S-isomer of Compound.

Other than Compound itself, none of the standard neuroleptics studied displaced [N-methyl-$^3$H] Compound at concentrations lower than those needed to displace at D-2 receptors.

These data show that Compound is unique among all the tested neuroleptics. It was 2500 times more potent in displacing [N-methyl-$^3$H] Compound than in displacing $^3$H-spiperone whereas all of the other neuroleptics were more potent in competing for $^3$H-spiperone binding sites. The data from these studies indicate that Compound binds stereospecifically with high affinity to a single site in rat striatum and suggest that this site is the D-1 receptor site.

The use of [N-methyl-$^3$H] Compound for studying D-1 receptor function in the future offers several advantages. Because of its strong specificity for what appear to be D-1 sites, D-2 sites are virtually unoccupied at the [N-methyl-$^3$H] Compound ligand concentration of 0.3 nM normally used in these assays. Consequently, in studying displacement from D-1 sites, it is not necessary to include spiperone in the assay to block D-2 binding as is done in assays with $^3$H-thioxanthenes. Other advantages include its lack of adsorption onto glass and plastic surfaces and low levels of non-specific relative to total binding. The recoverable radioactivity from the polypropylene tubes used in these experiments was found to be 97%. With respect to non-specific binding, at the normally employed [N-methyl-$^3$H] Compound ligand concentration of 0.3 nM, such binding constituted only 4–8% of total binding. For comparison non-specific binding of about 66% and 74% of total binding has been reported for $^3$H-piflutixol and $^3$H-flupentixol respectively [Life Sciences 23, 551 (1978)].

In conclusion, [N-methyl-$^3$H] Compound is an excellent probe for studying the D-1 dopamine receptor. Clear advantages over other radioligands currently used for this purpose include receptor specificity, low nonspecific binding and lack of adsorption onto assay tube surfaces.

Advantage may be taken of the unique D-1 binding properties of Compound to analyze for the concentration in the plasma of a psychotic patient, for example of an active neuroleptic drug known to have D-1 receptor antagonist properties.

Thus, a kit which contains a sample of purified rat brain membranes and an amount of radiolabeled Compound may be utilized to perform such a clinical analysis. A small plasma sample (less than 100 μl) can be used and the amount of radioactivity bound to brain membranes in the presence vs absence of plasma sample from a treated patient is the measure. The basic premise is that the amount of radioactivity displaced from brain receptors is proportional to the concentration of active drug in plasma which in turn determines therapeutic activity in Schizophrenia. The key to this assay is to have an active neuroleptic in radioactive form, with high specific activity (high radioactive counts/millimole of drug). A recent clinical reference [Psychopharmacology 82, 194 (1984)] further describes the outlined procedure.

All references herein disclosed are hereby incorporated by reference for their pertinent teachings.

We claim:

1. A method of analyzing a test compound for D-1 antagonistic activity comprising:
   (a) contacting mammalian brain tissue containing D-1 receptors with said test compound to form test compound D-1 receptor complexes;
   (b) adding tritiated R-(+)-8-chloro-2,3,4,5-tetrahydro-3-methyl-5-phenyl-1H-3-benzazepin-7-ol to the mammalian brain tissue;
   (c) measuring the amount of tritiated R-(+)-8-chloro-2,3,4,5-tetrahydro-3-methyl-5-phenyl-1H-3-benzazepin-7-ol complexed with D-1 receptors; and
   (d) correlating the amount of tritiated R-(+)-8-chloro-2,3,4,5-tetrahydro-3-methyl-5-phenyl-1H-3-benzazepin-7-ol complexed with said D-1 receptors to the level of said D-1 antagonism of said test compound.

2. A method of determining the level of D-1 antagonism of a neuroleptic drug in a plasma sample comprising:
   (a) contacting said plasma sample with mammalian brain tissue having D-1 receptor sites therein to form neuroleptic drug D-1 receptor complexes;
   (b) adding tritiated R-(+)-8-chloro-2,3,4,5-tetrahydro-3-methyl-5-phenyl-1H-3-benzazepin-7-ol to the mammalian brain tissue;
   (c) measuring the amount of tritiated R-(+)-8-chloro-2,3,4,5-tetrahydro-3-methyl-5-phenyl-1H-3-benzazepin-7-ol complexed with D-1 receptors; and
   (d) correlating the amount of tritiated R-(+)-8-chloro-2,3,4,5-tetrahydro-3-methyl-5-phenyl-1H-3-benzazepin-7-ol complexed with said D-1 receptors to the level of said D-1 antagonism of said neuroleptic drug.

* * * * *